US006258570B1

(12) United States Patent
Glustein et al.

(10) Patent No.: US 6,258,570 B1
(45) Date of Patent: Jul. 10, 2001

(54) PCR ASSAY FOR BACTERIAL AND VIRAL MENINGITIS

(75) Inventors: Joseph Z. Glustein; Garth D. Ehrlich; Yingze Zhang, all of Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/061,273

(22) Filed: Apr. 17, 1998

(51) Int. Cl.[7] .................. C12P 19/134; C12Q 1/68; C07H 21/04; C07H 21/00
(52) U.S. Cl. .................. 435/91.2; 435/6; 435/91.1; 536/23.7; 536/24.32; 536/25.32
(58) Field of Search .............. 435/6, 91.2, 91.1; 536/24.32, 23.7, 25.32

(56) References Cited

FOREIGN PATENT DOCUMENTS

90/02557 * 3/1990 (WO) ..................... A61K/35/66
90/11376 * 10/1990 (WO) ..................... C12Q/1/68

OTHER PUBLICATIONS

Pulli et al. Molecular comparison of coxsackie A virus serotypes, Virology vol. 212, p. 30–38, 1995.*
Dowson et al. Nucleotide sequence of the penicillin–binding protein 2B gene of *Streptococcus pneumoniae*, Nucleic acids research, vol. 17(18), p. 7518, 1989.*
Dowson et al. Horizontal transfer of penicillin–binding protein genes in penicillin–resistant clinical isolates of *Streptococcus pneumoniae*, Proc. Natl. Acad. Sci. USA, vol. 86, p. 8842–8846, 1989.*
Kammerer et al. Nested PCR for specific detection and rapid indentification of Human picornaviruses, J. Clin. Microbiol. vol. 32(2), p. 285–291, 1994.*
Edwards et al. Multiplex PCR: advantages, development, and applications (PCR methods and applications, S65–S75, 1994.*
Feigin, R.D., et al. *Textbook of Pediatric Infectious Diseases*, 3rd ed. (Eds) Cherry, J.D., W.B. Saunders Co., Phila. pp 439–445 (1992).
Radstrom, P., et al., *J. Clin. Microbiol. 32*: 2738 (1994).
Hall, L.M.C., et al., *Eur. J. Clin. Microbiol. Infect. Dis. 14*: 1090 (1995).
Rotbart, H.A., et al., *Clin. Inf. Dis. 20*: 971 (1995).
Abzug, M.J., et al., *J. Pediatr. 126*: 447 (1995).
Chapman, N.M., et al., *J. Clin. Microbiol. 28*: 843 (1990).
Rotbart, H.A., *J. Clin. Microbiol. 28*: 438 (1990).
Zoll, G.J., et al., *J. Clin Microbiol. 30*: 160 (1992).
Lina, B., et al., *J. Clin. Microbiol. 34*: 3007 (1996).
Yerly, S., et al., *J. Clin. Microbiol. 34*: 199 (1996).
Post, J.C., et al., *Molec. Diag. 1*:29 (1996).
Van Ketl, R.J., et al., *J. Med. Microbiol. 33*: 271 (1990).
Dowson, C.G., et al., *Proc. Natl. Acad. Sci. USA 87*: 5858 (1990).
Saunders, N.B., et al, *Gene 137*: 153 (1993).
Sirko, D.A., et al., *PCR–Based Diagnostics in Infectious Diseases*, Ehrlich, G.D., et al., (Eds) Blackwell Scientific publications, Boston, pp 19–43 (1994).
Ehrlich, G.D., et al., *PRC Protocols: A Guide To Methods and Applications*, Innis, M., et al., (Eds) Academic Priss, San Diego pp 325–336 (1990).
Ehrlich, G.D., et al, *Blood 74*: 1658 (1989).
Zhang, Y., et al., *J. Clin Microbiol. 33*: 596 (1995).

* cited by examiner

Primary Examiner—Eggerton A. Campbell
Assistant Examiner—J. Tung
(74) Attorney, Agent, or Firm—Reed Smith LLP

(57) ABSTRACT

A multiplex assay is provided for the simultaneous detection and discrimination of pathogens that cause bacterial and viral meningitis.

20 Claims, 5 Drawing Sheets

1 2 3 4      5 6 7 8      9 10 11 12

PCR ASSAY FOR BACTERIAL AND VIRAL MENINGITIS

ACKNOWLEDGMENT

The present invention was developed in part with government support under grant number DC02148 awarded by the National Institutes of Health. The government has certain rights in this invention.

FIELD OF THE INVENTION

The present invention relates generally to methods for clinically distinguishing between bacterial and viral meningitis. In particular, the present invention relates to a PCR-based multiplex assay for the rapid detection and discrimination of pathogens causing bacterial and viral meningitis.

BACKGROUND OF THE INVENTION

Bacterial meningitis is a neurologically devastating and often life threatening illness. Rapid and accurate diagnosis is therefore of utmost importance in providing timely and optimal care. In contrast, viral meningitis, which often presents with the same clinical signs and symptoms as bacterial meningitis, is a self-limiting illness that does not require antimicrobial treatment and hospitalization. See, Cherry, J. D., *Textbook of Pediatric Infectious Diseases*, 3rd ed. Feigin, R. D., et al. (Eds.) W.B. Saunders Co., Philadelphia, pp. 439–445 (1992), the disclosure of which is incorporated herein by reference.

Currently, physicians in the emergency room setting are repeatedly faced with the diagnostic dilemma of how to clinically distinguish between bacterial and viral meningitis. This feat is virtually impossible with any degree of certainty. Therefore, a patient is often hospitalized and treated with intravenous antibiotics until the results of bacterial cultures from the cerebrospinal fluid ("CSF") are determined. This process generally takes between 48 to 72 hours to complete. The waiting period can therefore result in a tremendous increase in health care costs and the provision of suboptimal care, particularly since greater than 90% of meningitis cases are of a viral etiology.

The use of microscopy in the diagnosis of bacterial meningitis lacks both specificity and sensitivity and further requiring a high titer of bacteria in the CSF. An additional complicating factor is that prior treatment of the patient with antibiotics can lead to a false-negative result of both gram-stain and culture from CSF. For these reasons, physicians are hesitant to rely on culture results and will opt to complete a full 10–14 day course of intravenous antibiotics which in the majority of cases is not necessary.

The potential benefits of the polymerase chain reaction ("PCR") technique to provide identification of a specific bacterial or viral etiology affects all patients by making this distinguishing information available in a relatively short period of time. A viable PCR-based assay has the potential to influence the clinician's decisions of how to institute treatment while the patient is still in the emergency room. Since a PCR-based method of detection does not depend on the presence of viable organisms but instead relies on genetic material, a PCR-based technique is applicable in all patient cases, even when antibiotics were administered prior to CSF specimen collection. Some difficulties, however, are associated with PCR-based methods, such as false-positive results due to contaminating nucleic acids and inhibition of the PCR reaction due to complex samples as detailed below.

PCR-based assays for bacterial and viral pathogens that cause meningitis have been developed in recent years. Radstrom, P., et al., *J. Clin, Microbiol*. 32: 2738 (1994) the disclosure of which is incorporated herein by reference, describes a PCR strategy for the simultaneous detection in CSF of *Neisseria meningitidis, Haemophilus influenzae, Streptococcus pneumoniae, Streptococcus agalactiae*, and eubacteria in general. Their assay showed a high sensitivity of 0.94 and specificity of 0.96 when tested on 304 clinical CSF samples. Their approach included the use of a nested PCR strategy to detect the various pathogens. This technique, however, increases the risk of contamination of the PCR reactants with amplicons because the reaction tubes have to be opened between PCR steps when using such a strategy. Similarly, Hall L. M. C., et al., *Eur. J. Clin. Microbial. Infect. Dis*. 14: 1090 (1995), the disclosure of which is incorporated herein by reference, describe a similar PCR-based assay for the detection of bacterial pathogens that cause meningitis. Once again, a nested PCR technique was used with its intrinsic shortcomings.

Enteroviruses currently account for 80%–92% of all cases of aseptic meningitis for which an etiologic agent is identified as reported by Rotbart, H. A., et al., *Clin. Inf. Dis*. 20: 971 (1995), the disclosure of which is incorporated herein by reference. Several reverse transcriptase ("RT")-PCR-based assays for the diagnosis for enteroviruses have been developed in recent years. See, for example, Abzug, M. J., et al., *J. Pediatr*. 126: 447 (1995); Chapman, N. M., et al., *J. Clin. Microbiol*. 28: 843 (1990); Rotbart, H. A., *J. Clin. Microbiol*. 28: 438 (1990); and Zoll, G. J., et al., *J. Clin. Microbiol*. 30: (1992), the disclosures of which are incorporated herein by reference. Lina, B., et al., *J. Clin. Microbiol*. 34: 302 (1996), the disclosure of which is incorporated herein by reference, report the use of a PCR-based assay to detect enteroviruses from cerebrospinal fluid. In that assay different concentrations of enteroviruses were artificially inoculated into sterile CSF and the CSF was analyzed using RT-PCR in 13 different laboratories. The RT-PCR assay was found to be more sensitive than cell culture for enteroviruses. Yerly, S., et al., *J. Clin. Microbiol*. 34: 199 (1996), the disclosure of which is incorporated herein by reference, compared the RT-PCR-based assay to viral cultures in 38 patients with aseptic meningitis. The rates of enterovirus detection were 66% by PCR and 34% by culture.

There remains a need, however, for a PCR-based assay that can simultaneously detect and discriminate between the pathogens that cause bacterial and viral meningitis which in addition to being rapid, is not prone to contamination and which has increased sensitivity and specificity over other methods.

The present invention provides a PCR-based multiplex assay for bacterial and viral meningitis which allows for rapid discriminatory diagnosis between the viral and bacterial types of meningitis and which can provide the foundation data for a diagnosis even after the institution of antimicrobial therapy.

SUMMARY OF THE INVENTION

Accordingly, it is a primary object of the present invention to provide a rapid assay for the simultaneous detection of the pathogens responsible for bacterial meningitis and viral meningitis.

Another object of the present invention is to provide a rapid assay for the simultaneous detection of the pathogens responsible for bacterial meningitis and viral meningitis that is not affected by prior treatment of the afflicted patient with antibiotics.

Still another object of the present invention is to provide a rapid assay for the simultaneous detection of the pathogens responsible for bacterial meningitis and viral meningitis that has increased sensitivity.

Another object of the present invention is to provide a multiplex PCR-based assay that can provide discriminatory diagnosis between bacterial and viral meningitis in children.

These and other objects of the present invention are achieved by one or more of the following embodiments.

In one aspect, the invention features a multiplex assay for the simultaneous detection and discrimination of pathogens that cause bacterial and viral meningitis in a patient, comprising:

obtaining cerebral spinal fluid from a patient suspected of being afflicted with bacterial or viral meningitis;

amplifying the most common pathogens that cause bacterial meningitis and viral meningitis in the cerebral spinal fluid by PCR technique using amplification primers for each of the common pathogens; and using labeled probes specific for a portion of the region amplified by the primers that can be detected to determine whether the bacterial or viral pathogens identified by each of the labeled probes is present in said sample.

In preferred embodiments the pathogens that cause bacterial meningitis in children comprise: *Neisseira meningitidis*, *Haemophilus influenzae*, and *Streptococcus pneumoniae* and the pathogen that causes viral meningitis in children comprises enteroviruses.

In another aspect, the invention features a kit for the simultaneous detection and discrimination of pathogens that cause bacterial and viral meningitis in a patient, comprising:

amplification primers for the pathogens *Neisseira meningitidis*, *Haemophilus influenzae*, and *Streptococcus pneumoniae*, and enteroviruses.

Other features and advantages of the invention will be apparent from the following description of the preferred embodiment, and from the claims.

DETAILED DESCRIPTION OF THE INVENTION

I. DEFINITIONS

Figure 1:
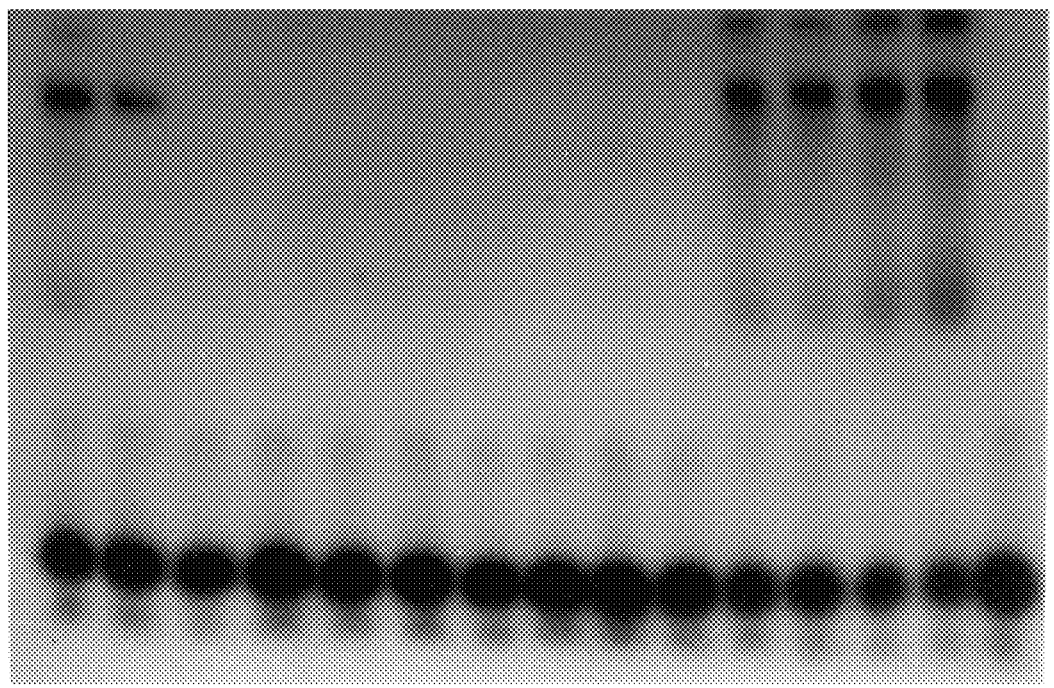
FIG. 1 is a photograph of an autoradiographic exposure from liquid hybridization-gel retardation analysis showing specificity panels of simplex PCR-based assays for *N. meningitidis* against different strains of the Neisseria species. Lanes 1–3 contain *N. meningitidis* (positive control-serial dilutions (only lanes 1, 2 are positive)); Lanes 4 and 15 are blank (no DNA); Lanes 5–6 contain *N. lactamica*; Lanes 7–8 contain *N. mucosa*; Lanes 9–10 contain *N. sicca*; Lanes 11–12 contain *N. gonorrhea*; and Lanes 13–14 contain *N. meningitidis*.

As used herein, "multiplex" means a PCR-based assay utilizing multiple primer and probe sets, where each primer/probe set is specific for one unique target DNA sequence.

"Simplex" means a PCR-based assay utilizing a primer and probe set specific for one unique target DNA sequence.

The term "amplimer" refers to the DNA product resulting from a PCR-based amplification of target DNA.

"Autoradiographic exposure" means a technique that uses x-ray film to visualize radioactively labeled molecules or fragments of molecules.

The term "detection system" as used herein refers to a method that enables visualization of PCR-amplified DNA products. Examples of suitable detection systems include systems that depend on radioactive exposure, fluorescence and chemiluminescence.

"Gel retardation analysis" means the separation of hybridized amplimer/probe product from unbound-labeled probe utilizing gel electrophoresis.

"Hybridization" refers to the process of joining two complementary strands of DNA to form a double-stranded molecule.

"Liquid hybridization" means the hybridization of complementary PCR amplimers and radioactively labeled probes in a liquid solution.

"Nucleotide" means a building block of DNA or RNA, consisting of one nitrogenous base, one phosphate molecule, and one sugar molecule (deoxyribose in DNA, ribose in RNA).

"Oligonucleotide" means a short string of nucleotides. Oligonucleotides are often used as probes to find a matching sequence of DNA or RNA and can be labeled with a variety of labels, such as radioisotopes and fluorescent and chemiluminescent moieties.

"Primer" means a short strand of oligonucleotides complementary to a specific target sequence of DNA which is used to prime DNA synthesis.

"Probe" means a specific sequence of single-stranded DNA used to seek out a complementary sequence of single-stranded DNA. Probes are usually labeled radioactively or chemically to make them easier to detect, thus revealing the target DNA sequence.

II. METHODS

According to the present invention a PCR-based multiplex assay for bacterial and viral meningitis is provided which provides rapid detection and discrimination between these two distinct diseases simultaneously. In the preferred embodiment set forth herein the assay is designed for detection of these two clinical entities in children (up to about age 17 or 18), but the invention is certainly not so limited and can be used and enhanced for use in adults.

The present invention demonstrates the ability to co-amplify the three most common pathogens that cause bacterial meningitis in children, namely *Neisseira meningitidis*; *Haemophilus influenzae*; and *Streptococcus pneumoniae* together with the major pathogen that causes viral meningitis, enteroviruses.

With the advent of PCR and other nucleic acid-based amplification strategies, infectious organisms can be identified from their unique DNA or RNA sequences. When designing an assay to differentially diagnose the etiologic agent causing a specific disease or syndrome, one must be able to potentially amplify several causative organisms simultaneously. The limitation of current simplex PCR-based assays is that only one specific organism can be detected per assay. Multiplex assays circumvent this by identifying one or more organisms simultaneously.

The use of a PCR-based multiplex assay for the diagnosis of meningitis has several advantages. The cerebrospinal fluid is a sterile environment. No organisms, pathogenic or otherwise, colonize in the cerebrospinal fluid except during active disease. This cannot be said of other body fluids such as saliva, sputum or gastrointestinal secretions. Therefore, the detection of an organism in the CSF by PCR is indicative of disease.

As mentioned above, clinicians are faced with a dilemma when deciding how to treat patients with meningitis, such as whether one should initiate intravenous antimicrobial therapy until culture results are available or whether the patient should be hospitalized for observation. If one diagnostic test could not only rule out bacterial etiologies of meningitis, but also positively diagnose a viral etiology, this would reassure the clinician of the cause of disease. This in turn would ensure that proper treatment was initiated at the outset and would alleviate the need for unnecessary and unwarranted medical care. The reduction in health care costs would be large. In addition, judicious use of antimicrobial therapy would lessen the likelihood of the development of resistant strains of bacteria.

Another advantage of the use of multiplex PCR-based testing for meningitis is in the not uncommon scenario when a patient has been given antibiotics prior to the collection of CSF. This is referred to as "partially treated" meningitis. One dose of antibiotics is sufficient to render the CSF as sterile by culture. However, the genetic material of the organism causing disease is still present and detectable days after initiation of therapy. This would render the PCR test to be positive in light of prior antimicrobial treatment. Hence, one would not be obligated to complete a full course of antimicrobial treatment just because the cultures are unreliable.

In summary, the PCR-based multiplex assay for *H. influenzae, S. pneumoniae, N. meningitidis* and enteroviruses has been demonstrated to be both sensitive and specific for the detection of the four target organisms causing the majority of cases of meningitis in children.

The multiplex assay of the present invention was accordingly designed to take into consideration several factors which in general cause difficulties for such types of assays. See, for example, Post, J. C., et al., *Molec. Diag.* 1: 29 (1996), the disclosure of which is incorporated herein by reference.

For example, design criteria for a multiplex PCR-based assay for use in a clinical setting include the following:

a rational approach for the inclusion or exclusion of specific pathogens in the assay. In the present invention, for example, the assay for detection of the pathogens that cause bacterial and viral meningitis in children employs amplification primers and detection probes for *N. meningitidis, H. influenzae, S. pneumoniae*, and enteroviruses. A panel useful for diagnosis of meningitis in adults would employ primers/probes for the following organisms which are the primary ones causing meningitis in adults: *H. influenzae, S. pneumoniae, N. meningitidis*, gram-negative bacilli, Streptococci, Staphylococci, and Listeria species.

the use of broadly inclusive primers must be used to ensure the identification of all strains of the particular target species involved as is the case in the present invention.

the use of a single-step amplification process which precludes the need for nested primers and reamplification. Reamplification must be avoided due to the fact that aerosolization of the primary amplimer can occur during addition of nested primers, resulting in carry-over which can result in a false positive result.

the use of compatible primers for all the component primer sets so that there is no interference or cross-reactivity among them. Any primer dimerization or false binding between or among the various sets of primer pairs and target DNA's can decrease the sensitivity of the assay. In the present invention the oligonucleotide primers are about 18–30 nucleotides long.

the maintenance of sensitivity in the multiplex assay as compared with the component simplex assays. To obtain such a result, all primer pairs are to be designed to work under the same assay conditions. For example, cycling conditions that are optimal for one primer set may not be ideal for another primer set. The use of one set of cycling conditions for all the organisms involved in the present assay will necessitate other changes in the assay parameters. The assay should also be validated by using both serial dilutions of known DNAs and clinical specimens.

easily and clearly resolvable amplification products. This can be achieved in several ways, such as consideration of amplimer length, individual target capture positions, or discrete reporter groups. The present detection method used takes into account several considerations: amplimer length, predetermined optimal site of hybridization between PCR product and probe (which influences the migration of the hybridized product in gel electrophoresis) and conditions of gel electrophoresis such as the nature and composition of the gel matrix, applied voltage, and duration of electrophoresis.

Other detection systems that may also be used in accordance with the present invention include the utilization of fluorescence and chemiluminescene. An example of fluorescence is the discreet fluorescent dye labeling of probes in order to differentiate between amplimers in a PCR-based multiplex assay. Presently, one of the current systems utilizing chemiluminescence is a homogenous quantum coupled real-time chemiluminescent assay. This technique is currently widely used for the detection of widely varying target DNA sequences. With this technique, the detection process occurs simultaneously during the amplification process, significantly shortening the duration of the assay. Additionally, the assay allows for quantitative detection of the specific target DNA.

The present invention of a PCR-based multiplex assay for bacterial and viral meningitis provides for rapid discriminatory diagnosis between these two types of pathogens simultaneously in patients, and in the preferred embodiment, in children. As will be demonstrated below, the methods of the present invention allows for co-amplification of the three most common pathogens that cause bacterial meningitis in children, namely, *Neisseria meningitidis, Haemophilus influenzae* and *Streptococcus pneumoniae* together with the major pathogen causing viral meningitis, namely, enteroviruses. Kits containing the preferred primers and probes may also be provided according to the present invention. It will be appreciated that other similar primers and probes are also within the scope of the present invention.

Advantages of the present assay include inclusivity, such that simultaneous detection of multiple organisms is enabled, increased sensitivity and specificity, and rapidity in obtaining an accurate diagnosis. With current advances in PCR technology, it is now feasible that the laboratory turnaround time from acquisition of the clinical sample to interpretation of the result would be approximately two hours. Therefore in the future the decision making process in the emergency room would be influenced by the results of the assay of the present invention, and the treatment and disposition of the patient would be altered. This in turn will obviate the necessity for hospitalizing the majority of patients with meningitis, providing the opportunity to institute appropriate medical therapy and drastically reduce health care costs.

The following example is provided by way of illustration and is in no way intended to limit the scope of the present invention in any way.

EXAMPLE

Primer Synthesis for Polymerase Chain Reaction

The OLIGO™ primer analysis software program (National Biosciences, Plymouth, Minn.) was used as an aid in the design of amplification primers and probes. All primers and probes were synthesized using standard β-cyanoethyl phosphoramidite chemistry on an Applied Biosystems Inc. ("ABI") (Foster City, Calif.) model 391 or 392 synthesizers. Oligonucleotides were purified by reverse-phase chromatography using OLIGO™ purification cartridges (ABI). The resulting oligonucleotides were then vacuum centrifuged to dryness, resuspended in 1×TE (10-mmol/l TRIS-HCl (pH 7.5) and 1-mmol/l $Na_2EDTA$), and were quantitated by ultraviolet absorption spectrophotometry at 260 nm. All primers and probes were diluted to 10 pmol/μl in TE buffer and stored at −20° C.

In the preferred embodiment, PCR-based assays were developed for *H. influenzae, S. pneumoniae*, and *N. meningitidis* and the genus enterovirus, which are the most common pathogenic organisms that cause bacterial and viral meningitis in children. Primers and probes for all three bacterial pathogens and enteroviruses were designed from on-line DNA sequences (GenBank) or were taken directly from the literature. The sequences for the primers and probes of these pathogens are given in Table 1 below:

TABLE 1

Sequences for primers and probes for *Neisseria meningitidis, Haemophilus influenzae*, enteroviruses and *Strepococcus pneumoniae*

| Primer | Probe | Gene | Sequence Nos. | Sequence (5'-3') | Amplimel Size |
|---|---|---|---|---|---|
| *Neisseria meningitidis* | | | | | |
| NM12 (+) | | porA | 319-342 | CCC AAA ACA GCA AGT CCG CCT ATA (SEQ ID NO:1) | |
| | NM16 (+) | porA | 593-627 | TGA CGG GCG GCT ATG AGG AAG GCG GCT TGA ATC TC (SEQ ID NO:2) | 384 bp 384 bp |
| NM15 (−) | | porA | 702-679 | AGT GGC GGC AAT TTC GGT CGT ACT (SEQ ID NO:3) | |
| *Haemophilus influenzae* | | | | | |
| HI-4 (+) | | P6 | 103-122 | ACT TTT GGC GGT TAC TCT GT (SEQ ID NO:4) | |
| | HI-6B (+) | P6 | 123-152 | TGC TGA TCT TCA ACA ACG TTA CCA TAC CGT (SEQ ID NO:5) | |
| HI-5 (−) | | P6 | 375-356 | TGT GCC TAA TTT ACC AGC AT (SEQ ID NO:6) | |
| Enterovirus | | | | | |
| MD-90 (−) | | 5'NTR | 603-584 | ATT GTC ACC ATA AGC AGC CA (SEQ ID NO:7) | |
| | EVP (+) | 5'NTR | 568-539 | GAA ACA CGG ACA CCC AAA GTA GTC GGT TCC GCC ACG GAC (SEQ ID NO:8) | 154 bp |
| MD-91 (+) | | 5'NTR | 450-474 | CCT CCG GCC CCT GAA TGC GGC TAAT (SEQ ID NO:9) | |

TABLE 1-continued

Sequences for primers and probes for Neisseria meningitidis, Haemophilus influenzae, enteroviruses and Strepococcus pneumoniae

| Primer | Probe | Gene | Sequence Nos. | Sequence (5'-3') | Amplimel Size |
|---|---|---|---|---|---|
| Streptococcus pneumoniae | | | | | |
| JM201 (+) | | PBP2B | 1805-1825 | ATG CAG TTG GCT CAG TAT GTA (SEQ ID NO:10) | |
| | JM204 (+) | PBP2B | 1836-1865 | CA ATT ATT GGT GTT CGT GTG GCT CCT CGT A (SEQ ID NO:11) | 87 bp |
| JM202 (−) | | PBP2B | 1891-1872 | CAC CCA GTC CTC CCT TAT CA (SEQ ID NO:12) | |

The H. influenzae primer-probe set (HI-4/HI-5-HI-6B), (SEQ ID NO: 4; SEQ ID NO: 6; and SEQ ID NO: 5, respectively) was derived from the DNA sequence coding for the outer membrane protein P6. See, Van Ketl, R. J., et al., *J. Med. Microbiol.* 33: 271 (1990); Dowson, C. G., et al., *Proc. Natl. Acad. Sci. USA* 87: 5858 (1990); Saunders, N. B., et al., *Gene* 137: 153 (1993); and Sirko, D. A., et al., *PCR-Based Diagnostics In Infectious Disease*, Ehrlich, G. D., et al., (Eds.) Blackwell Scientific publications, Boston pp. 19–44 (1994), the disclosures of which are incorporated herein by reference. The S. pneumoniae primer-probe set (JM201/JM202-JM204), (SEQ ID NO: 10; SEQ ID NO: 12; and SEQ ID NO: 11, respectively) was designed from the penicillin-binding protein 2B ("PBP2B") gene based on the published sequence as reported by Dowson, C. G., et al., *Proc. Natl. Acad. Sci. USA* 87: 5858 (1990) the disclosures of which are incorporated herein by reference. The N. meningitidis primer-probe set (NM12/NM15-NM16) (SEQ ID NO: 1; SEQ ID NO: 3; and SEQ ID NO: 2, respectively) was derived from the DNA sequence coding for the class 1 outer membrane protein ("porA") as reported by Saunders, N. B., et al., *Gene* 137: 153 (1993), the disclosures of which are incorporated herein by reference. A specific primer-probe set (MD-90/MD-91-EVP) (SEQ ID NO: 7; SEQ ID NO: 9; and SEQ ID NO: 8, respectively) was designed from the published sequence of the enteroviruses See, Rotbart, H. A., et al., *J. Clin. Microbiol.* 28: 438 (1990), the disclosure of which is incorporated herein by reference and used to detect the cDNA of enteroviruses reverse-transcribed from serial dilutions of a viral stock.

Polymerase Chain Reaction

All amplifications were performed in a volume of 100 µl. A 2×PCR master mix of reaction buffer (1×=50 mM KCl; 10 mM Tris (pH 8.3); 2.5 mM $MgCl_2$; 0.2 mM (each) dATP, dCTP, dGTP, dUTP (Pharmacia, Piscataway, N.J.) 2 Units of Taq polymerase (Perkin-Elmer, Norwalk, Conn.); and 10 pmol of each of the primers was adjusted to a volume of 50 µl with sterile water. 10 µl aliquots of extracted DNA were adjusted to a volume of 50 µl with water, and combined with 50 µl of the above-referenced master mix to produce a 100 µl volume for the PCR reaction. Thermal cycling was performed in a Model 9600 thermal cycler (Perkin-Elmer). Standard cycling conditions included an initial 10-minute denaturation step at 94° C., followed by 35 cycles with a 1 minute denaturation step at 94° C., a 1 minute primer annealing step at 55° C., and an extension step of 1 minute at 72° C. A 10-minute extension at 72° C. was included at the end of the final cycle. The PCR products were stored at 4° C. is prior to analysis.

Liquid Hybridization-Gel Retardation Analysis of Amplification Products

Radioactive labeling of the internal oligonucleotide probes (HI-6B, JM204, NM16 and EVP) (SEQ ID NO: 5; SEQ ID NO: 11; SEQ ID NO: 2; and SEQ ID NO: 8, respectively) was accomplished by using T4 polynucleotide kinase (New England Biolabs; Beverly, Mass.) and ($\gamma^{32}$-P) ATP (3000 ci/mmol specific activity), as described by Ehrlich, G. D., et al., *PCR protocols: A Guide to Methods and Applications*, in Innis, M., et al., (Eds.) Academic Press, San Diego pp. 325–336 (1990), the disclosure of which is incorporated herein by reference.

The amplified DNA was hybridized in solution with $^{32}P$ end-labeled oligonucleotide probes complementary to one of the strands of each target amplification sequence. For the multiplex assay, a single hybridization cocktail was prepared which contained 250,000 counts per minute ("cpm") of each of the four end-labeled oligonucleotide probes. The read-out system employed for all simplex and multiplex-generated amplification products was gel retardation of the hybridization products followed by autoradiography. See, Ehrlich, G. D., et al., in Innis, M., et al., (Eds.) *PCR Protocols: A Guide to Methods and Applications*, Academic Press, San Diego pp. 325–336 (1990) and Ehrlich, G. D., et al., *Blood* 74: 1658 (1989), the disclosures of which are incorporated herein by reference.

III. RESULTS

Sensitivity and Specificity

The simplex PCR-based assay for H. influenzae was able to reproducibly support detectable amplification from an input of 10 fg of bacterial genomic DNA (3–7 genomic equivalents). The simplex S. pneumoniae assay was able to consistently support amplification from an input of 100 fg of bacterial genomic DNA and in some instances from an input of 10 fg. The simplex N. meningitidis assay was able to support amplification from an input of 100 fg of bacterial genomic DNA. The simplex enteroviral assay was able to support amplification from $10^5$ dilutions of cDNA.

Figure 2:
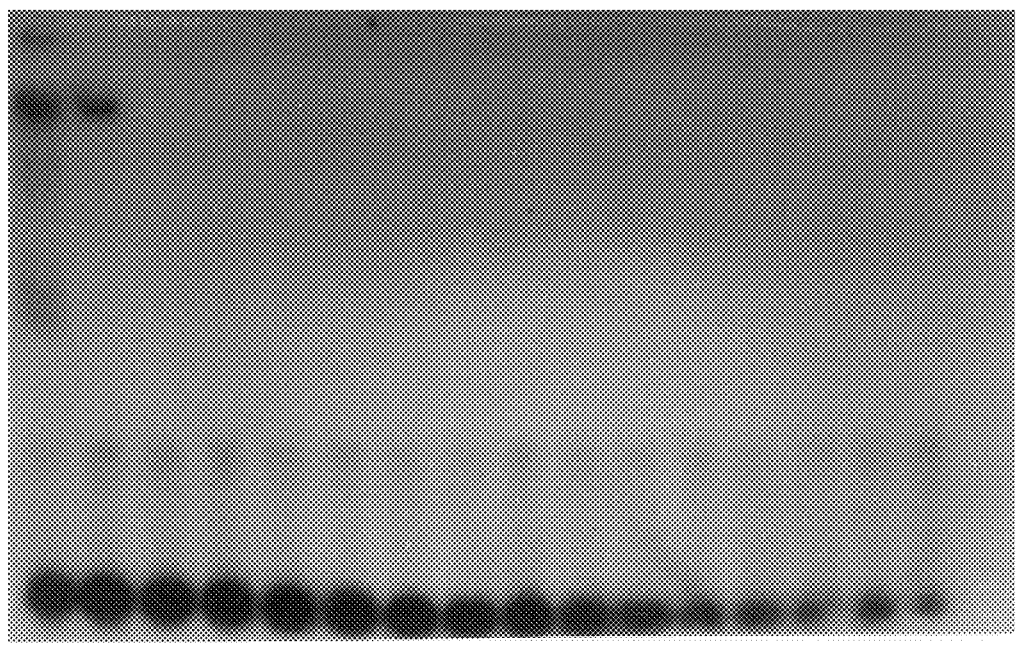
FIG. 2 is photograph of an autoradiographic exposure from liquid hybridization-gel retardation analysis showing specificity panels of simplex PCR-based assays for *N. meningitidis* against gram-negative bacterial organisms. Lanes 1–2 contain *N. meningitidis* (positive control); Lanes 3 and 16 are blank (no DNA); Lanes 4–5 contain *E. coli*; Lanes 6–7 contain Acinetobacter species; Lanes 8–9 contain *P. aeruginosa*; Lanes 10–11 contain *M. catarrhalis*; Lanes 12–13 contain *H. influenzae* type B; and Lanes 14–15 contain *H. parainfluenzae*.
Figure 3:
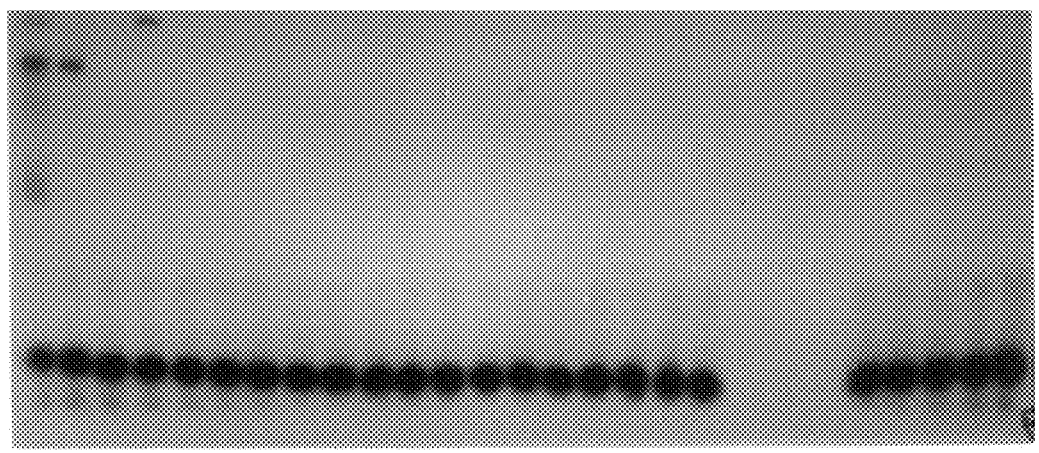
FIG. 3 is a photograph of an autoradiographic exposure from liquid hybridization-gel retardation analysis showing specificity panels of simplex PCR-based assays for *N. meningitidis* against the DNAs purified from gram-positive bacterial organisms, yeast, and human sources. Lanes 1–2 contain *N. meningitidis* (positive control): Lanes 3, 12, 19, and 24 are blank (no DNA); Lanes 4–5 contain group A Streptococcus; Lanes 6–7 contain group C Streptococcus; Lanes 8–9 contain Enterococcus; Lanes 10–11 contain *S. viridans*; Lanes 13–14 contain *S. epidermidis*; Lanes 15–16 contain *S. aureus*; Lanes 17–18 contain *S. pneumoniae*; Lanes 20–21 contain *C. albicans*; and Lanes 22–23 contain human DNA.

The S. pneumoniae assay was demonstrated to be capable of supporting amplification from a battery of 51 strains, including 15 serotypes and both penicillin-sensitive and penicillin-resistant isolates. See, Zhang, Y., et al., *J. Clin. Microbiol.* 33: 596 (1995), the disclosure of which is incorporated herein by reference. All strains of H. influenzae that were examined, including type B and nontypable isolates, were detected. Similarly, the simplex assay for N. meningitidis was able to support all strains of N. meningitidis and N. gonorrhea, but not commensal non-pathogenic bacteria Neisseria such as N. lactamica, N. sicca, and N. mucosa as seen in FIG. 1. None of the species-specific amplification-detection systems for N. meningitidis evidenced any cross-reactivity when tested with a panel of DNA samples extracted from human pathogens, commensal bacteria and yeast sources as seen in FIGS. 2–3. Specificity of the enteroviral assay has been seen in previous studies by Rotbart, H. A., et al. When tested against herpes simplex virus, cytomegalovirus and respiratory syncytial virus, the present assay showed no amplification.

Development of the Multiplex Assay

Figure 4:
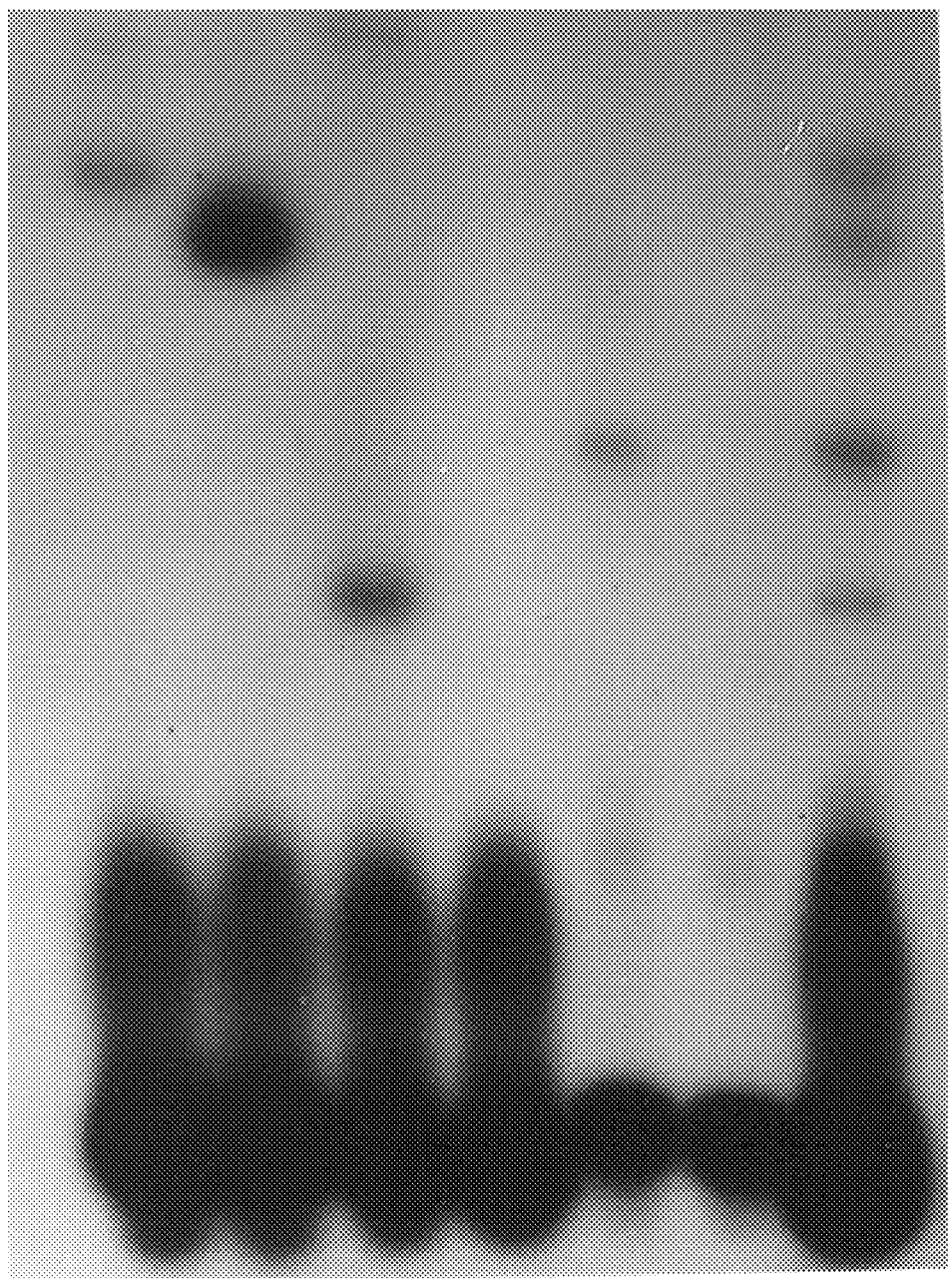
FIG. 4 is a photograph of an autoradiographic exposure from liquid hybridization-gel retardation analysis showing a specificity panel of multiplex PCR-based amplification of *N. meningitidis*, *H. influenzae*, *S. pneumoniae* and enterovirus DNAs. Lane 1 contains *N. meningitidis*; Lane 2 contains *H. influenzae*; Lane 3 contains *S. pneumoniae*; Lanes 4 and 6 are blank (no DNA); Lane 5 contains enterovirus DNAs; Lane 7 contains input DNA from all four organisms and shows amplification of all four organisms simultaneously.
Figure 5:
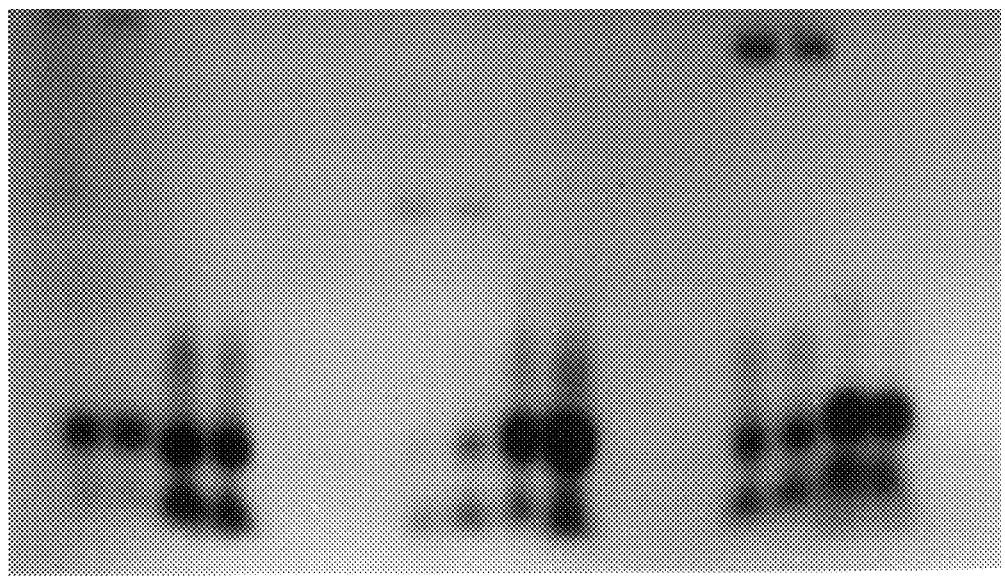
FIG. 5 is a photograph of an autoradiographic exposure from liquid hybridization-gel retardation analysis demonstrating specificity between liquid hybridization probes and simplex PCR-based amplification of *N. meningitidis*, *H. influenzae*, and *S. pneumoniae*. Input DNA: Lanes 1–4 contain *N. meningitidis*; Lanes 5–8 contain *S. pneumoniae*; Lanes 9–12 contain *H. influenzae*. Probes: Lanes 1–2 contain *N. meningitidis*; Lanes 3–4 contain *H. influenzae*, and *S. pneumoniae*; Lanes 5–6 contain *S. pneumoniae*; Lanes 7–8 contain *N. meningitidis* and *H. influenzae*; Lanes 9–10 contain *H. influenzae*; and Lanes 11–12 contain *S. pneumoniae* and *N. meningitidis*.

When each of the four simplex assays were combined into one multiplex assay, the result was the co-amplification of four distinct amplimer products. Hybridization of the products simultaneously with a mixture of the four corresponding radio-labeled probes resulted in four separate bands that were distinguishable from each other on gel retardation analysis as seen in FIG. 4. Combining the assays into a multiplex form did not compromise sensitivity. Additionally, there was no evidence of cross-reactivity between the primers and probes of the various species as seen in FIG. 5.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A multiplex assay for the simultaneous detection and discrimination of pathogens that cause bacterial and viral meningitis in a patient, comprising:
   obtaining a sample of cerebrospinal fluid from a patient suspected of being afflicted with bacterial or viral meningitis;
   amplifying the most common pathogens that cause bacterial meningitis and viral meningitis in said sample of cerebrospinal fluid by PCR technique using amplification primers for each of said common pathogens, said primers comprising NM12 (SEQ ID NO: 1), NM15 (SEQ ID NO: 3), HI-4 (SEQ ID NO: 4), HI-5 (SEQ ID NO: 6), JM201 (SEQ ID NO: 10), JM202 (SEQ ID NO: 12), MD-90 (SEQ ID NO: 7), and MD-91 (SEQ ID NO: 9); and
   using labeled probes specific for a portion of the region amplified by said primers that can be detected to determine whether the bacterial or viral pathogens identified by each of said labeled probes is present in said sample of cerebrospinal fluid, said probes comprising NM16 (SEQ ID NO: 2), HI-6B (SEQ ID NO: 5), JM204 (SEQ ID NO: 11), and EVP (SEQ ID NO: 8).

2. The assay of claim 1, wherein said patient is a child.

3. The assay of claim 2, wherein said pathogens that cause bacterial meningitis in children comprise: *Neisseira meningitidis, Haemophilus influenzae,* and *Streptococcus pneumoniae.*

4. The assay of claim 2, wherein said pathogen that causes viral meningitis in children is enteroviruses.

5. The assay of claim 3, wherein the primers for *Neisseira meningitidis* consist of NM12 (5'-CCC AAA ACA GCA AGT CCG CCT ATA-3') (SEQ ID NO: 1) and NM15 (5'-AGT GGC GGC AAT TTC GGT CGT ACT-3') (SEQ ID NO: 3).

6. The assay of claim 3, wherein the primers for *Haemophilus influenzae* consist of HI-4 (5'-ACT TTT GGC GGT TAC TCT GT-3') (SEQ ID NO: 4) and HI-5 (5'-TGT GCC TAA TTT ACC AGC AT-3') (SEQ ID NO: 6).

7. The assay of claim 3, wherein the primers for *Streptococcus pneumoniae* consist of JM201 (5'-ATG CAG TTG GCT CAG TAT GTA-3') (SEQ ID NO: 10) and JM202 (5'-CAC CCA GTC CTC CCT TAT CA-3') (SEQ ID NO: 12).

8. The assay of claim 4, wherein the primers for enteroviruses consist of MD-90 (5'-ATT GTC ACC ATA AGC AGC CA-3') (SEQ ID NO: 7) and MD-91 (5'-CCT CCG GCC CCT GAA TGC GGC TAA T-3') (SEQ ID NO: 9).

9. The assay of claim 3, wherein the probe for *Neisseira meningitidis* consists of NM16 (5'-TGA CGG GCG GCT ATG AGG AAG GCG GCT TGA ATC TC-3') (SEQ ID NO: 2).

10. The assay of claim 3, wherein the probe for *Haemophilus influenzae* consists of HI-6B (5'-TGC TGA TCT TCA ACA ACG TTA CCA TAC CGT-3') (SEQ ID NO: 5).

11. The assay of claim 3, wherein the probe for *Streptococcus pneumoniae* consists of JM204 (5'-CA AAT AAT GGT GTT CGT GTG GCT CCT CGT A-3') (SEQ ID NO: 11).

12. The assay of claim 3, wherein the probe for enteroviruses consists of EVP (5'-GAA ACA CGG ACA CCC AAA GTA GTC GGT TCC GCC ACG GAC-3') (SEQ ID NO: 8).

13. The method of claim 1, wherein said probes are radioactively labeled.

14. The method of claim 1, wherein said labeled amplified product is detected by liquid hybridization-gel retardation analysis.

15. The assay of claim 1, wherein said patient is an adult.

16. The assay of claim 15, wherein said pathogens are selected from the group consisting of *H. influenzae, S. pneumoniae, N. meningitidis*, gram-negative bacilli, Streptococci, Staphylococci, and Listeria species.

17. A kit for the simultaneous detection and discrimination of pathogens that cause bacterial and viral meningitis in a patient, comprising:

amplification primers for the pathogens *Neisseria meningitidis*, NM12 (SEQ ID NO: 1) and NM15 (SEQ ID NO: 3), *Haemophilus influenzae*, HI-4 (SEQ ID NO: 4) and HI-5 (SEQ ID NO: 6), and *Streptococcus pneumoniae*, JM201 (SEQ ID NO: 10) and JM202 (SEQ ID NO: 12) and enteroviruses, MD-90 (SEQ ID NO: 7) and MD-91 (SEQ ID NO: 9).

18. The kit of claim 17, further comprising probes for each of said pathogens, wherein said probes comprise NM 16 (SEQ ID NO: 2), HI-6B (SEQ ID NO: 5), JM204 (SEQ ID NO: 11), and EVP (SEQ ID NO: 8).

19. The kit of claim 17, wherein:

the primers for *Neisseira meningitidis* consist of NM12 (5'-CCC AAA ACA GCA AGT CCG CCT ATA-3') (SEQ ID NO: 1) and NM15 (5'-AGT GGC GGC AAT TTC GGT CGT ACT-3') (SEQ ID NO: 3);

the primers for *Haemophilus influenzae* consist of HI-4 (5'-ACT TTT GGC GGT TAC TCT GT-3') (SEQ ID NO: 4) and HI-5 (5'-TGT GCC TAA TTT ACC AGC AT-3') (SEQ ID NO: 6);

the primers for *Streptococcus pneumoniae* consist of JM201 (5'-ATG CAG TTG GCT CAG TAT GTA-3') (SEQ ID NO: 10) and JM202 (5'-CAC CCA GTC CTC CCT TAT CA-3') (SEQ ID NO: 12); and the primers for enteroviruses consist of MD-90 (5'-ATT GTC ACC ATA AGC AGC CA-3') (SEQ ID NO: 7) and MD-91 (5'-CCT CCG GCC CCT GAA TGC GGC TAA T-3') (SEQ ID NO: 9).

20. The kit of claim 17, wherein:

the probe for *Neisseira meningitidis* consists of NM16 (5'-TGA CGG GCG GCT ATG AGG AAG GCG GCT TGA ATC TC-3') (SEQ ID NO: 2);

the probe for *Haemophilus influenzae* consists of HI-6B (5'-TGC TGA TCT TCA ACA ACG TTA CCA TAC CGT-3') (SEQ ID NO: 5);

the probe for *Streptococcus pneumoniae* consists of JM204 (5'-CA AAT AAT GGT GTT CGT GTG GCT CCT CGT A-3') (SEQ ID NO: 11) and the probe for enteroviruses consists of EVP (5'-GAA ACA CGG ACA CCC AAA GTA GTC GGT TCC GCC ACG GAC-3') (SEQ ID NO: 8).

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH:24 nucleotides
      (B) TYPE:nucleic acid
      (C) STRANDEDNESS:single
      (D) TOPOLOGY:linear (ii) MOLECULE TYPE:synthetic DNA (iii) SEQUENCE DESCRIPTION: SEQ ID NO: 1:

CCCAAAACAG CAAGTCCGCC TATA                                      24

(2) INFORMATION FOR SEQ ID NO:2:

(i) SEQUENCE CHARACTERISTICS:
      (A) LENGTH: 35 nucleotides
      (B) TYPE:nucleic acid
      (C) STRANDEDNESS:single
      (D) TOPOLOGY:linear (ii) MOLECULE TYPE:synthetic DNA (iii) SEQUENCE DESCRIPTION:SEQ ID NO: 2:

TGACGGGCGG CTATGAGGAA GGCGGCTTGA ATCTC                         35

(2) INFORMATION FOR SEQ ID NO:3:

(i) SEQUENCE CHARACTERISTICS:
      (A) LENGTH: 24 nucleotides
      (B) TYPE:nucleic acid
      (C) STRANDEDNESS:single
      (D) TOPOLOGY:linear (ii) MOLECULE TYPE:synthetic DNA (iii) SEQUENCE DESCRIPTION:SEQ ID NO: 3:

AGTGGCGGCA ATTTCGGTCG TACT                                      24

(2) INFORMATION FOR SEQ ID NO:4:

(i) SEQUENCE CHARACTERISTICS:
      (A) LENGTH: 20 nucleotides
      (B) TYPE:nucleic acid
      (C) STRANDEDNESS:single
      (C) TOPOLOGY:linear (ii) MOLECULE TYPE:synthetic DNA (iii) SEQUENCE DESCRIPTION:SEQ ID NO: 4:

```
ACTTTTGGCG GTTACTCTGT                                                    20

(2) INFORMATION FOR SEQ ID NO:5:

(i) SEQUENCE CHARACTERISTICS:
        (A) LENGTH:   30 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 5:

TGCTGATCTT CAACAACGTT ACCATACCGT                                         30

(2) INFORMATION FOR SEQ ID NO:6:

(i) SEQUENCE CHARACTERISTICS:
        (A) LENGTH:   20 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 6:

TGTGCCTAAT TTACCAGCAT                                                    20

(2) INFORMATION FOR SEQ ID NO:7:

(i) SEQUENCE CHARACTERISTICS:
        (A) LENGTH:   20 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 7:

ATTGTCACCA TAAGCAGCCA                                                    20

(2) INFORMATION FOR SEQ ID NO:8:

(i) SEQUENCE CHARACTERISTICS:
        (A) LENGTH:   39 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 8:

GAAACACGGA CACCCAAAGT AGTCGGTTCC GCCACGGAC                                39

(2) INFORMATION FOR SEQ ID NO:9:

(i) SEQUENCE CHARACTERISTICS:
        (A) LENGTH:   25 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 9:

CCTCCGGCCC CTGAATGCGG CTAAT                                              25
```

```
-continued (2) INFORMATION FOR SEQ ID NO:10:

(i) SEQUENCE CHARACTERISTICS:
        (A) LENGTH:  21 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 10:

ATGCAGTTGG CTCAGTATGT A                                      21

(2) INFORMATION FOR SEQ ID NO:11:

(i) SEQUENCE CHARACTERISTICS:
        (A) LENGTH:  30 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 11:

CAAATAATGG TGTTCGTGTG GCTCCTCGTA                             30

(2) INFORMATION FOR SEQ ID NO:12:

(i) SEQUENCE CHARACTERISTICS:
        (A) LENGTH:  20 nucleotides
        (B) TYPE:nucleic acid
        (C) STRANDEDNESS:single
        (C) TOPOLOGY:linear (ii) MOLECULE TYPE:synthetic DNA (iii) SEQUENCE DESCRIPTION:SEQ ID NO: 12:

CACCCAGTCC TCCCTTATCA                                        20
```